US00PP19137P3

(12) United States Plant Patent
Harrison et al.

(10) Patent No.: US PP19,137 P3
(45) Date of Patent: Aug. 26, 2008

(54) RASPBERRY PLANT NAMED 'DRISCOLL ESTRELLA'

(50) Latin Name: *Rubus idaeus*
Varietal Denomination: Driscoll Estrella

(75) Inventors: Rick Harrison, Aptos, CA (US); Fred Cook, Aptos, CA (US); Brian Hamilton, San Jose, CA (US); Gavin Sills, Watsonville, CA (US)

(73) Assignee: Driscoll Strawberry Associates, Inc.

( * ) Notice: Subject to any disclaimer, the term of this patent is extended or adjusted under 35 U.S.C. 154(b) by 221 days.

(21) Appl. No.: 11/327,109

(22) Filed: Jan. 6, 2006

(65) Prior Publication Data

US 2007/0163014 P1 Jul. 12, 2007

(51) Int. Cl.
*A01H 00/05* (2006.01)

(52) U.S. Cl. ..... Plt./204

(58) Field of Classification Search ..... Plt./204
See application file for complete search history.

*Primary Examiner*—Wendy C. Haas
*Assistant Examiner*—Georgia Helmer
(74) *Attorney, Agent, or Firm*—Jones Day

(57) ABSTRACT

The present invention relates to a new and distinct cultivar of raspberry plant named 'Driscoll Estrella'. The new cultivar is distinguished from other raspberry cultivars by its yellow fruit color, fruit firmness, consistent fruit structure and high yield. The new cultivar is distinguished from its pollen parent by producing a higher yield of larger, firmer fruit with a brighter yellow color.

3 Drawing Sheets

1. LATIN NAME OF THE GENUS AND SPECIES OF THE PLANT CLAIMED

The variety is botanically identified as *Rubus idaeus* L. subgenus *Rubus*.

1.2 VARIETY DENOMINATION

The Raspberry variety denomination is 'Driscoll Estrella'.

2. BACKGROUND OF THE INVENTION

This invention relates to a new cultivar of raspberry called 'Driscoll Estrella'. The new cultivar of raspberry plant was developed from a single seedling selected from the hybridization of the selection Q481.7 (an unpatented variety) as the seed parent with the selection S826.3 (an unpatented variety) as the pollen parent. The parents were crossed in 1998, whereafter fruit and seed were collected to produce seedlings for field planting in Watsonville, Calif. in 1998. The new cultivar was selected from these seedlings in 2000 for its yellow color, productivity and flavor. The cultivar has been asexually propagated by in vitro shoot tip culture, root sucker division and root cuttings at the Cassin Ranch in Santa Cruz County, Calif. and has been shown to maintain the desired and distinguishing characteristics after propagation over several generations.

3. SUMMARY OF THE INVENTION

The present invention provides a new and distinct yellow raspberry cultivar named 'Driscoll Estrella'. The cultivar is botanically identified as *Rubus idaeus* L. The 'Driscoll Estrella' yellow raspberry plant produces a primocane crop which begins in late June and continues until early November. The floricane crop begins in late April and continues until late June or early July. Both the primocane and floricane yields are high relative to other comparable yellow varieties. The fruit of 'Driscoll Estrella' is notably quite firm and very consistent with regard to its size and shape throughout its harvest period. The fruit of 'Driscoll Estrella' separates easily from its receptacle.

4. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics. The specimens in FIGS. 1–3 are about 11 months old.

5. DETAILED BOTANICAL DESCRIPTION

Figure 1:
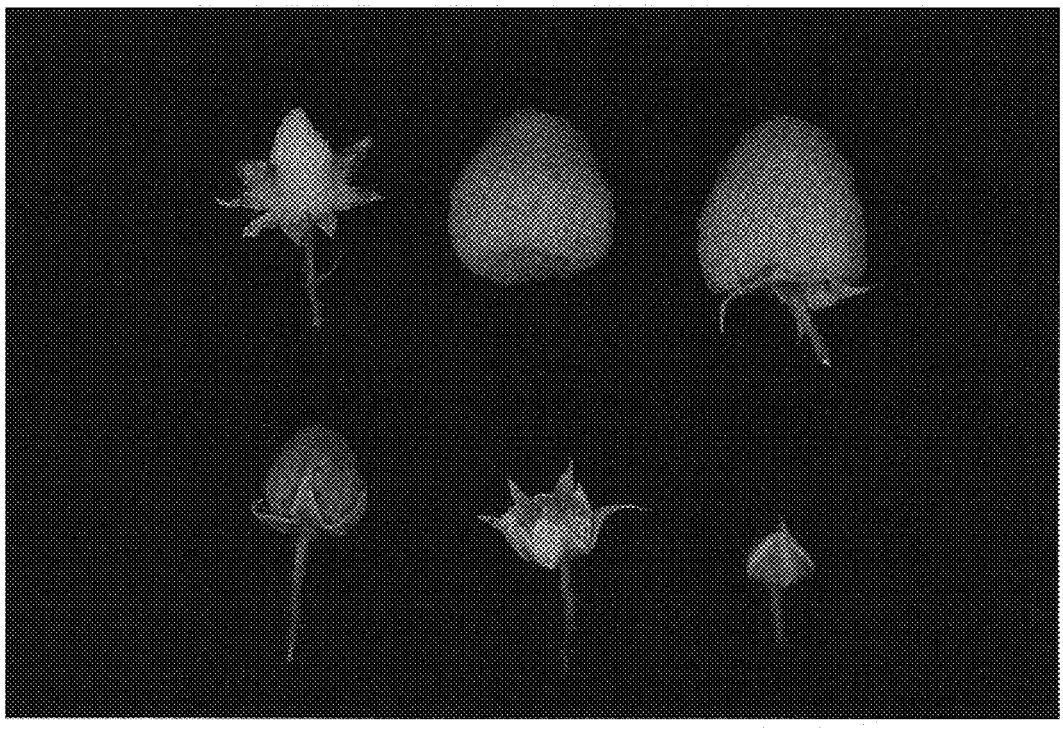
FIG. 1 is a photograph of 'Driscoll Estrella' primocane flower and fruit in various stages of development.
Figure 2:
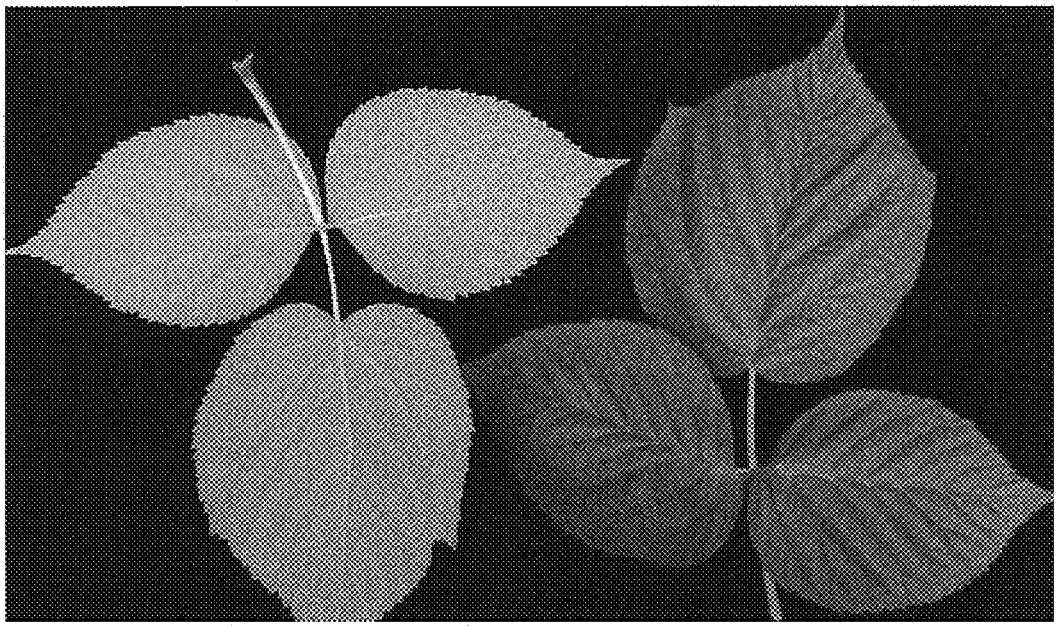
FIG. 2 is a photograph of 'Driscoll Estrella' primocane leaves showing upper and lower leaf surfaces.
Figure 3:
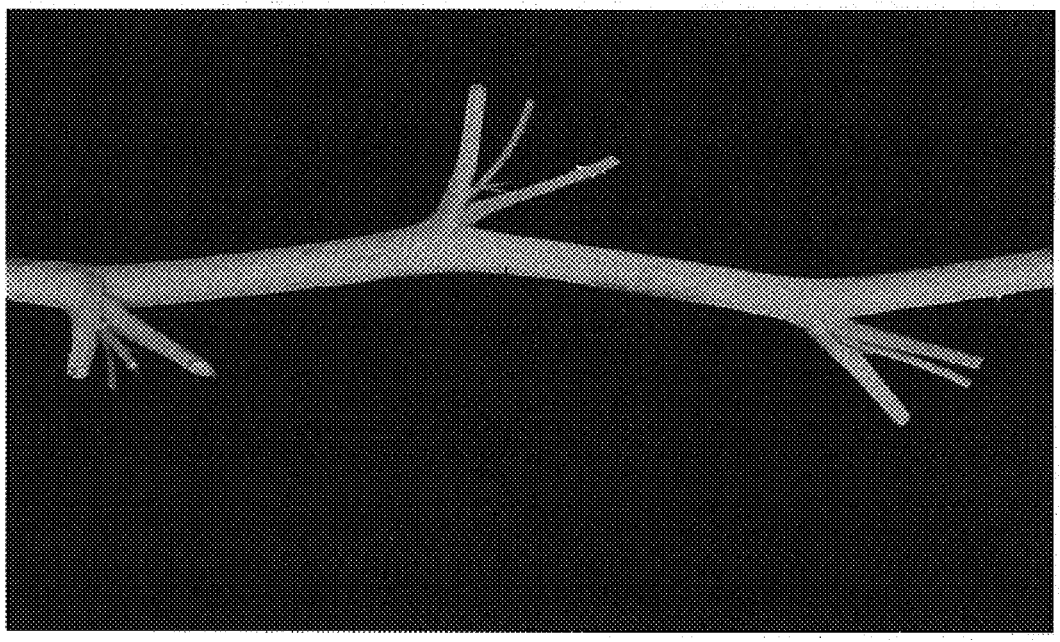
FIG. 3 is a photograph of 'Driscoll Estrella' primocane shoot.

The following detailed description of the new raspberry cultivar, 'Driscoll Estrella', is based upon observations taken of plants and fruit grown in Watsonville, Calif. between 2001 and 2005, and is believed to apply to plants of the 'Driscoll Estrella' cultivar grown in similar conditions of soil and climate elsewhere.

Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by the Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Estrella' compared with characteristics of the unpatented raspberry cultivar 'Heritage'. Observations of the cultivars were taken in comparisons under similar conditions.

The new variety is particularly characterized and distinguished from other cultivars by its yellow fruit color, fruit firmness, consistent fruit structure and high yield. The fruit color of 'Driscoll Estrella' is a bright yellow at harvest. Fruit of 'Driscoll Estrella' separates easily from the receptacle and is of excellent firmness at harvest. The fruit of 'Driscoll Estrella' is very consistent in size and shape throughout the harvest period.

The primocane and floricane yields of 'Driscoll Estrella' are high relative to the variety 'Heritage'. 'Driscoll Estrella' is distinguishable from its pollen parent, selection 'S826.3', by producing a higher yield of larger, firmer fruit with a brighter yellow color. The new cultivar has similar fruit size, shape and color as its seed parent, selection 'Q481.7'. Additional characteristics of 'Driscoll Estrella' include an average flower diameter of about 10.0 mm.

5.1 DISEASE AND STRESS RESISTANCE

'Driscoll Estrella' has exhibited some resistance to Phragmidium rust and Phytophthora root rot. Cold tolerance of the new cultivar has not been established. Post harvest fruit rot resistance is good in comparison with many selections and varieties.

TABLE 1

PLANT CHARACTERISTICS OF 'DRISCOLL ESTRELLA'

| | Driscoll Estrella | Heritage |
|---|---|---|
| GENERAL | | |
| Plant Size | Small to medium | Large |
| Growth habit | Erect | Erect |
| Productivity | High | Medium |
| Self-fruitfulness | Self-fruitful | Self-Fruitful |
| Time of bud burst | Medium | Medium |
| Primocane fruiting | | |
| Percent of cane | 50-70 | 20-40 |
| Length flowering as Primocane | | |
| Percent of total yield | 51 | 50 |
| Primocanes | | |
| Number of young shoots | Many | Medium |
| Young shoot pigmentation | None | Medium |
| Length (cm) | 178 | 195 |
| Time of shoot emergence | Early | Medium |
| Glaucosity (waxy bloom) | Weak | Weak |
| Strength | Medium | Medium |
| Cane cross section (from mid cane of primocane) | Angular | Rounded to angular |
| Dormant cane color | 164-A | 166-B |
| Prickles | | |
| Pigmentation | Green | Green to brown-green |
| Density on young shoots | Medium | Dense |
| Attitude of tip | Horizontal | Downward |
| Size | Medium | Medium |
| Size: Length (mm) (base to tip at 1 m height at end of harvest) | 1.8 | 2.0 |
| Texture | Heavy | Heavy |
| Presence and distribution of petioles | Present, regularly distributed | Present, regularly distributed |
| Pubescence on canes | Absent | Absent |

TABLE 1-continued

PLANT CHARACTERISTICS OF 'DRISCOLL ESTRELLA'

| | Driscoll Estrella | Heritage |
|---|---|---|
| Internodal distance (cm) (at central ⅓ of cane) | 4.8 | 4.3 |
| LEAVES | | |
| Color | | |
| Face | 147-A | 147-A |
| Underside | N138-C | 148-C |
| Relief between veins | Medium | Weak |
| Glossiness | Medium | Medium |
| Petiole | | |
| Length (cm) | 7.3 | 7.0 |
| Pigmentation of upper surface | Absent | Present |
| Pigmentation of underside | Absent | Absent |
| Stipule orientation | Reflex | Erect |
| Arrangement | Compound | Compound |
| Number of leaflets | Sometimes 3, Sometimes 5 | Sometimes 3, sometimes 5 |
| Overlapping of lateral leaflets | Touching | Free to touching |
| Lateral leaflet: length to stalklet (lower pair) | Very short | Very short |
| Terminal leaflet | | |
| Length (cm) | 12.6 | 14.8 |
| Width (cm) | 10.0 | 8.8 |
| Shape | Ovate | Ovate |
| Tip | Acuminate | Acuminate |
| Base | Cordate | Rounded |
| Margin | Doubly serrate | Doubly serrate |
| Lateral leaflets (basal pair) | | |
| Length (cm) | 10.7 | 13.7 |
| Width | 7.3 | 7.8 |
| Orientation | Opposite | Opposite |
| Shape | Ovate | Ovate |
| Tip | Acuminate | Acuminate |
| Base | Oblique | Oblique |
| Margin | Doubly serrate | Doubly serrate |
| Rachis length between terminal leaflet and adjacent lateral leaflet (cm) | 2.1 to 4.4 | 3.7 to 5.8 |
| FLOWERS | | |
| Flowering period | | |
| Primocane | Late May to late September | Early July to Early October |
| Floricane | Early April to Mid June | Mid April to Mid June |
| Flower size | Medium | Medium |
| Petal | | |
| Length (cm) | 0.9 | 0.7 |
| Width (cm) | 0.5 | 0.3 |
| Pedicel | | |
| Coloration | None | Medium |
| Length | Medium | Medium |
| FRUIT | | |
| Harvest Season | | |
| Primocane | Late June to Late October | Early August to Early November |
| Floricane | Early May to Mid July | Late May to Mid July |

TABLE 1-continued

PLANT CHARACTERISTICS OF 'DRISCOLL ESTRELLA'

| | Driscoll Estrella | Heritage |
|---|---|---|
| Fruiting Lateral | | |
| Number of fruit per lateral | 14 | 23 |
| Color | Yellow | Medium Red |
| Immature | 11-B | 180-A |
| Maturing | 162-B | 185-B |
| Mature fruit | 162-A | 185-A |
| Glossiness | Medium | Medium |
| Shape | Ovate | Ovate |
| Dimensions | | |
| Size | Medium | Small |
| Length (mm) | 22 | 19 |
| Width (mm) | 23 | 19 |
| Length:width | 0.95 | 1.0 |
| Weight (g/Fruit) | | |
| Primocane | 4.5 | 3.4 |
| Floricane | 4.4 | 2.6 |
| Soluble Solids (%) | 11.1 | 10.5 |
| Titratable acidity (% as citric acid) | 1.3 | 1.50 |
| Seeds | | |
| Weight (mg/seed) | 1.87 | 1.62 |
| Number druplets/fruit | 82 | 75 |
| Adherence to plug (1-9) | Medium | Medium |
| Firmness | Very firm | Firm |
| Yield | High | Medium |

What is claimed:

1. A new and distinctive cultivar of raspberry plant, substantially as shown and described.

* * * * *